(12) United States Patent
Drori et al.

(10) Patent No.: US 9,526,623 B2
(45) Date of Patent: Dec. 27, 2016

(54) SPINAL DISC ANNULUS CLOSURE DEVICE

(71) Applicant: NEWVERT LTD., Netanya (IL)

(72) Inventors: Hagay Drori, Tel Aviv (IL); Hamid Sharim, Kokhav Yair (IL); Roey Shafrir, Modi'in (IL); Gil Naor, Hofit (IL); Boaz Harari, Ganei Tikva (IL)

( * ) Notice: Subject to any disclaimer, the term of this patent is extended or adjusted under 35 U.S.C. 154(b) by 27 days.

(21) Appl. No.: 14/403,181

(22) PCT Filed: Dec. 5, 2012

(86) PCT No.: PCT/IL2012/050508
§ 371 (c)(1),
(2) Date: Nov. 23, 2014

(87) PCT Pub. No.: WO2013/179277
PCT Pub. Date: Dec. 5, 2013

(65) Prior Publication Data
US 2015/0094815 A1  Apr. 2, 2015

Related U.S. Application Data

(60) Provisional application No. 61/652,880, filed on May 30, 2012, provisional application No. 61/697,838, filed on Sep. 7, 2012.

(51) Int. Cl.
*A61F 2/44* (2006.01)
*A61F 2/46* (2006.01)
(Continued)

(52) U.S. Cl.
CPC ........... *A61F 2/442* (2013.01); *A61B 17/0057* (2013.01); *A61F 2/4611* (2013.01);
(Continued)

(58) Field of Classification Search
CPC ............ A61F 2/442; A61F 2002/30062; A61F 2002/30064; A61F 2002/30092; A61F 2002/30329; A61F 2002/30579; A61F 2002/30598; A61F 2002/30599; A61F 2002/30677; A61F 2002/4435; A61F 2002/4495; A61F 2002/30617; A61F 2/4611; A61F 2002/30571; A61B 17/0057; A61B 2017/00592; A61B 2017/00623; A61B 2017/00628; A61B 2017/00871; A61B 2017/00889; A61B 2017/00893
(Continued)

(56) References Cited

U.S. PATENT DOCUMENTS

| | | | |
|---|---|---|---|
| 3,788,327 A | 1/1974 | Donowitz et al. | |
| 6,371,990 B1 | 4/2002 | Ferree | |

(Continued)

FOREIGN PATENT DOCUMENTS

| | | |
|---|---|---|
| WO | 03/039328 A2 | 5/2003 |
| WO | 2004/069026 A2 | 8/2004 |

(Continued)

OTHER PUBLICATIONS

International Search Report for PCT/IL2012/050508 issued by European Patent Office on Apr. 10, 2013.
(Continued)

*Primary Examiner* — Pedro Philogene
(74) *Attorney, Agent, or Firm* — Simon Kahn; Chanoch Kahn

(57) ABSTRACT

An implant (300) for repair of a spinal inter-vertebral disc, constituted of a first section and a second section, each having: a support member section (110); a proximal support member secured to the proximal end of the support member section and arranged to extend proximally thereof, the proximal support member (170) arranged in a deployed configuration to distend in the direction of the first face (130)
(Continued)

of the support member section (110); and a pair of one inter-annulus support members (170), each of the pair of inter-annulus support members optionally exhibiting a plurality of stacked layers, arranged so as to cooperating under ejection forces to act as a single layer, the support member section of the first section secured to the support member section of the second section such that the second face of the first section faces the second face of the second section.

26 Claims, 11 Drawing Sheets

(51) Int. Cl.
    *A61B 17/00*     (2006.01)
    *A61F 2/30*     (2006.01)

(52) U.S. Cl.
    CPC ............ *A61B 2017/00592* (2013.01); *A61B 2017/00623* (2013.01); *A61B 2017/00628* (2013.01); *A61B 2017/00871* (2013.01); *A61B 2017/00889* (2013.01); *A61B 2017/00893* (2013.01); *A61F 2002/30062* (2013.01); *A61F 2002/30064* (2013.01); *A61F 2002/30092* (2013.01); *A61F 2002/30329* (2013.01); *A61F 2002/30571* (2013.01); *A61F 2002/30579* (2013.01); *A61F 2002/30598* (2013.01); *A61F 2002/30599* (2013.01); *A61F 2002/30617* (2013.01); *A61F 2002/30677* (2013.01); *A61F 2002/4435* (2013.01); *A61F 2002/4495* (2013.01); *A61F 2310/00017* (2013.01); *A61F 2310/00023* (2013.01); *A61F 2310/0097* (2013.01); *A61F 2310/00796* (2013.01); *A61F 2310/00976* (2013.01)

(58) Field of Classification Search
    USPC .................. 623/17.11–17.16; 606/246–279
    See application file for complete search history.

(56) References Cited

U.S. PATENT DOCUMENTS

| | | | |
|---|---|---|---|
| 6,425,924 B1 | 7/2002 | Rousseau | |
| 6,508,839 B1 | 1/2003 | Lambrecht et al. | |
| 6,676,665 B2 * | 1/2004 | Foley | A61B 17/025 600/201 |
| 6,805,695 B2 | 10/2004 | Keith et al. | |
| 7,004,970 B2 | 2/2006 | Cauthen, III et al. | |
| 7,033,395 B2 | 4/2006 | Cauthen | |
| 7,060,089 B2 | 6/2006 | Ley et al. | |
| 7,198,047 B2 | 4/2007 | Lambrecht et al. | |
| 7,223,289 B2 | 5/2007 | Trieu et al. | |
| 7,326,200 B2 | 2/2008 | Trieu et al. | |
| 7,503,936 B2 | 3/2009 | Trieu | |
| 7,615,076 B2 | 11/2009 | Cauthen, III et al. | |
| 7,658,765 B2 | 2/2010 | Lambrecht et al. | |
| 7,670,380 B2 | 3/2010 | Cauthen, III | |
| 7,799,058 B2 | 9/2010 | Froehlich et al. | |
| 7,828,850 B2 | 11/2010 | Cauthen, III et al. | |
| 7,857,857 B2 | 12/2010 | Kim | |
| 7,867,278 B2 | 1/2011 | Lambrecht et al. | |
| 7,905,923 B2 | 3/2011 | Keith et al. | |
| 7,959,679 B2 | 6/2011 | Lambrecht et al. | |
| 2002/0123807 A1 * | 9/2002 | Cauthen, III | A61F 2/441 623/17.12 |
| 2002/0156530 A1 | 10/2002 | Lambrecht et al. | |
| 2003/0144695 A1 | 7/2003 | McGuckin, Jr. et al. | |
| 2003/0153976 A1 | 8/2003 | Cauthen, III et al. | |
| 2004/0024463 A1 | 2/2004 | Thomas, Jr. et al. | |
| 2004/0260305 A1 | 12/2004 | Gorensek et al. | |
| 2005/0267524 A1 | 12/2005 | Chanduszko | |
| 2006/0217747 A1 | 9/2006 | Ferree | |
| 2006/0247776 A1 | 11/2006 | Kim | |
| 2007/0073337 A1 * | 3/2007 | Abbott | A61B 17/0057 606/213 |
| 2007/0162131 A1 | 7/2007 | Friedman et al. | |
| 2007/0198021 A1 | 8/2007 | Wales | |
| 2007/0232992 A1 | 10/2007 | Kutsko et al. | |
| 2007/0233252 A1 | 10/2007 | Kim | |
| 2008/0071301 A1 | 3/2008 | Matsuura et al. | |
| 2010/0004664 A1 | 1/2010 | Boyajian et al. | |
| 2010/0179641 A1 | 7/2010 | Ryan et al. | |
| 2010/0185287 A1 | 7/2010 | Allard et al. | |
| 2010/0204797 A1 | 8/2010 | Lambrecht et al. | |
| 2011/0009904 A1 | 1/2011 | Froehlich et al. | |
| 2011/0029001 A1 | 2/2011 | Trieu et al. | |
| 2011/0118844 A1 | 5/2011 | Lambrecht | |
| 2011/0125271 A1 | 5/2011 | Lambrecht et al. | |
| 2011/0172682 A1 | 7/2011 | Brady et al. | |

FOREIGN PATENT DOCUMENTS

| | | | |
|---|---|---|---|
| WO | 2004/093729 A2 | 11/2004 | |
| WO | 2007/011994 A2 | 1/2007 | |
| WO | WO2007/011994 A3 * | 1/2007 | ............ A61F 2/442 |
| WO | 2010/081033 A1 | 7/2010 | |
| WO | 2010/089717 A1 | 8/2010 | |
| WO | 2010/141910 A2 | 12/2010 | |
| WO | 2012/120509 A1 | 9/2012 | |

OTHER PUBLICATIONS

Written Opinion of the International Searching Authority for PCT/IL2012/050508 issued by European Patent Office on Apr. 10, 2013.

* cited by examiner

| | |
|---|---|
| 2000 | ADD ADDITIVE TO IMPLANT, OPTIONALLY A PORTION OF THE IMPLANT IS IMPREGNATED, OR COATED, WITH THE ADDITIVE, OPTIONALLY THE ADDITIVE IS COUPLED TO A PORTION OF THE IMPLANT, OPTIONALLY A PORTION OF THE IMPLANT IS DESIGNED TO CARRY AND DELIVER THE ADDITIVE TO ADJACENT TISSUE |
| 2010 | (OPT.) ADDITIVE COMPRISES A DIAGNOSTIC AGENT, OPTIONALLY COMPRISING A RADIO-OPAQUE MATERIAL SUITABLE TO PERMIT IMAGING BY X-RAY OR MRI |
| 2020 | (OPT.) ADDITIVE COMPRISES ONE OR MORE THERAPEUTIC AGENTS, OPTIONALLY ONE OF: ANTIBIOTICS; ANTIPROLIFERATIVE, CYTOTOXIC, AND ANTITUMOR DRUGS INCLUDING CHEMOTHERAPEUTIC DRUGS; ANALGESIC; ANTIANGIOGEN; ANTIBODY; ANTIVIRALS; CYTOKINES; COLONY STIMULATING FACTORS; PROTEINS; CHEMOATTRACTANTS; EDTA; HISTAMINE; ANTIHISTAMINE; ERYTHROPOIETIN; ANTIFUNGALS; ANTIPARASITIC AGENTS; NON-CORTICOSTEROID ANTI-INFLAMMATORY AGENTS; ANTICOAGULANTS; ANESTHETICS; ANALGESICS; ONCOLOGY AGENTS; CARDIOVASCULAR DRUGS; VITAMINS AND OTHER NUTRITIONAL SUPPLEMENTS; HORMONES; GLYCOPROTEINS; FIBRONECTIN; PEPTIDES INCLUDING POLYPEPTIDES AND PROTEINS; INTERFERONS; CARTILAGE INDUCING FACTORS; PROTEASE INHIBITORS; VASOCONSTRICTORS, VASODILATORS, DEMINERALIZED BONE OR BONE MORPHOGENETIC PROTEINS; LIPIDS; CARBOHYDRATES; PROTEOGLYCANS; ANTIANGIOGENINS; ANTIGENS; DBM; HYALURONIC ACID AND SALTS AND DERIVATIVES THEREOF; POLYSACCHARIDES; CELLULOSE COMPOUNDS AND DERIVATIVES THEREOF; ANTIBODIES; GENE THERAPY REAGENTS; GENETICALLY ALTERED CELLS, STEM CELLS INCLUDING MESENCHYMAL STEM CELLS WITH TRANSFORMING GROWTH FACTOR, AND/OR OTHER CELLS; CELL GROWTH FACTORS; TYPE II COLLAGEN; ELASTIN; SGAG; GLUCOSAMINE SULFATE; PH MODIFIERS; MSM; OSTEOGENIC COMPOUNDS; OSTEOCONDUCTIVE COMPOUNDS; PLASMINOGEN; NUCLEOTIDES; OLIGONUCLEOTIDES; POLYNUCLEOTIDES; POLYMERS; OP-1, INCLUDING RECOMBINANT OP-1; LMP-1; CARTILAGE; OXYGEN-CONTAINING COMPONENTS; ENZYMES; MELATONIN; VITAMINS; AND NUTRIENTS |
| 2030 | (OPT.) ADDITIVE COMPRISES APROTININ AND CALCIUM IONS |
| 2040 | (OPT.) ADDITIVE COMPRISES ANTI-INFLAMMATORY AGENT OPTIONALLY COMPRISING INHIBITORS OF PLURALITY OF CYTOKINES OPTIONALLY ONE OF: IL-1; IL-6;IL-8; TNF-A; AND METALLOPROTEINASES, OPTIONALLY AGENT ONE OF: TNF OR ILANTAGONISTS; AND ANTI-INFLAMMATORY NUTRACEUTICALS. |
| 2050 | (OPT.) ADDITIVE COMPRISES GROWTH FACTORS, OPTIONALLY ONE OF: TRANSFORMING, INSULIN-LIKE, OR PLATELET-DERIVED GROWTH FACTORS; BMP-2; BMP-7; AND GDF5 |

FIG. 8

SPINAL DISC ANNULUS CLOSURE DEVICE

FIELD OF THE INVENTION

The invention relates generally to the field of implantable devices for the repair and closure of a spinal invertebral disc defect, and more particularly to an implant arranged to securely seal an invertebral disc defect with improved anti-ejection characteristics.

BACKGROUND OF THE INVENTION

The human spine, known technically as the vertebral column, is constituted of a plurality of articulating vertebrae, and extending downwards towards fused vertebrae in the sacrum and coccyx. Using standard anatomical terminology, the vertebral column is found in the dorsal aspect of the torso. The articulating vertebrae are separated from adjacent vertebrae on either side by an invertebral disc which forms a cartilaginous joint to allow slight movement of the vertebrae, and further acts to hold the various vertebrae together so as to form the vertebral column.

Each invertebral disc comprises an outer annulus fibrosus, often simply called the annulus, which surrounds and contains the nucleus pulposus which is a jelly-like substance which functions to distribute hydraulic pressure within each invertebral disc under compressive loads. In the event of an invertebral disc defect, such as a prolapsed or herniated disc, the nucleus pulposus is forced out through the defect of the annulus, and may apply pressure to nearby nerves or to the spinal cord. In severe cases the escaping nucleus pulposus may cause chemical irritation of nearby nerve roots. Protrusion of the nucleus pulposus may be variously referred to as a disc bulge, a herniated disc, a ruptured disc or a sequestered disc, depending on the specific diagnosis.

In order to avoid confusion in describing medical devices, certain fixed terminology is utilized. In particular, the term proximal usually means closer to the surgeon, unless otherwise stated, and the word distal usually means further removed from the surgeon, unless otherwise stated. Surgery to repair a defect in the annulus is usually performed from the patient's dorsal side, i.e. from the back, and thus the terms proximal and distal are understood with the surgeon approaching from the patient's back; however this is not meant to be limiting in any way. In the event of surgery performed ventrally, the terms need to be understood in relation to a dorsal operation.

While various schemes for repair of the annulus defects are known, one common solution is a surgical procedure known as discectomy which involves the surgical removal of the herniated disc material. Discectomy is often performed in conjunction with a laminectomy, where a small piece of bone, known as the lamina, is removed from the affected vertebra, allowing the surgeon to better see and access the area of disc herniation.

One problem with the above procedure is that additional nucleus pulposus material may be ejected from the annulus over time by the unsealed defect in the annulus, which is not sealed by the discectomy. Thus, a device and associated procedure is required to seal the annulus defect. Various devices and procedures are known to the prior art, including without limitation, WIPO Patent Publication S/N WO 2010/089717 entitled "Implantable Device for Sealing a Spinal Annular Fissure Tear and Method for Deploying the Same", the entire contents of which are incorporated herein by reference. One issue not fully addressed by the above subject patent publication, and other devices of the prior art, is the issue of ejection, i.e. the tendency of any device placed in the annulus to be ejected over time responsive to forces developed in the remaining nucleus pulposus material.

Certain improved devices are described in WIPO Patent Publication S/N WO 2012/120509 entitled "Spinal Disc Annulus Closure Device", the enter contents of which are incorporated herein by reference, based on a tubular format. One of the challenges of such a device is to stand up to strong hydrostatic ejection forces of up to 20 atmospheres while not interfering with a full range of motion of the vertebral column. Unfortunately, such a tubular format experiences difficulty with repeated sagittal flex and extension.

What is desired, and not supplied by the prior art, is a device arranged to: seal the annulus against further release of nucleus pulposus material through the defect; resist ejection from the annulus; allow for a full range of motion of the vertebral column over an expected patient lifetime without fatigue failure; and be easily manipulated to an insertion size.

SUMMARY

Accordingly, it is a principal object of the present invention to overcome at least some of the disadvantages of the prior art. In certain embodiments this is provided by an implant for repair of a spinal inter-vertebral disc, the implant comprising: a first section and a second section, each of the first section and the second section comprising: a support member section exhibiting a longitudinal axis, the support member section having a first face and a second face opposing the first face, the support member further having a distal end and a proximal end; a proximal securing member secured to the proximal end of the support member section and arranged to extend proximally thereof, the proximal securing member arranged in a deployed configuration to distend in the direction of the first face of the support member section; and a pair of inter-annulus support members, each of the pair of inter-annulus support members arranged on opposing sides of the longitudinal axis of the support member section along the proximal end, each of the pair of inter-annulus support members exhibiting a first end secured to the proximal end of the support member section, a second end and a link member coupling the first end to the second end, each of the inter-annulus support members having a deployed configuration wherein the second end of each of the inter-annulus support members extends away from the longitudinal axis of the axial support member section, a first face of each of the inter-annulus support members generally facing the support member section and generally concavingly curved when viewed from the proximal end of the support member section, and a second face of each of the inter-annulus support members generally convexingly curved when viewed from the proximal end of the support member section, the support member section of the first section secured to the support member section of the second section such that the second face of the first section faces the second face of the second section.

In one further embodiment each of the pair of inter-annulus support members comprises a plurality of stacked layers, each of the plurality of stacked layers exhibiting a first end secured to the proximal end of the support member section, a second end and a link member coupling the first end to the second end, wherein in the deployed configuration a first face of each of the inter-annulus support member layers generally faces the support member section and is generally concavingly curved when viewed from the proximal end of the support member section, and a second face of each of the inter-annulus support members is generally convexingly curved when viewed from the proximal end of the support member section. In one yet further embodiment, at least one of the plurality of stacked layers further comprising a protrusion at the second thereof arranged so as to arrest movement of an adjacent layer, at a predetermined point, caused by a force applied to the adjacent layer, the protrusion provided member and the adjacent layer layers thus cooperating under the force to act as a single layer.

In one further embodiment the proximal support member is constituted of a unitary member. In another further embodiment the proximal securing member comprises an extending portion, which in the deployed configuration distends in the direction of the first face of the support member section. In one yet further embodiment the support member sections, inter-annulus support members and proximal support member occlude 20%-95% of a target channel in a spinal annulus.

In one further embodiment the second face of the support member section of the first section is arranged to meet the second face of the support member of the second section. In another further embodiment the support member section of the first section comprises an elastic member arranged to extend past the second surface of the support member section of the first section, the support member section of the second section secured to a far face of the elastic member of the first section the elastic member providing elasticity to support Sagittal motion when deployed.

In one further embodiment the support member section of each of the first section and the second section comprises an elastic member arranged to extend past the second surface of the support member section of the respective section, a far face of the elastic member of the first section secured to a far face of the elastic member of the second section, the elastic members providing elasticity to support Sagittal motion when deployed. In another further embodiment each of the inter-annulus support members has a delivery configuration wherein the inter-annulus support members do not extend past a plane defined by the outer surfaces of the support member section. In one yet further embodiment the proximal securing member exhibits a delivery configuration wherein the proximal securing member does not extend past a plane defined by the outer surfaces of the support member section. In one further embodiment, the implant is formed from a bio-compatible shape memory polymer.

In another further embodiment the implant further comprises an additive, the additive coupled to a portion of the implant, coated on a portion of the implant or impregnated into a portion of the implant. Optionally, the additive comprises a diagnostic agent such as a radio-opaque material. Optionally, the additive comprises a therapeutic agent, which further optionally is selected from the group consisting of: antibiotics; antiproliferative, cytotoxic, and antitumor drugs including chemotherapeutic drugs; analgesic; antiangiogen; antibody; antivirals; cytokines; colony stimulating factors; proteins; chemoattractants; ethylenediaminetetraacetic acid (EDTA); histamine; antihistamine; erythropoietin; antifungals; antiparasitic agents; non-corticosteroid anti-inflammatory agents; anticoagulants; anesthetics; analgesics; oncology agents; cardiovascular drugs; vitamins and other nutritional supplements; hormones; glycoproteins; fibronectin; peptides including polypeptides and proteins; interferons; cartilage inducing factors; protease inhibitors; vasoconstrictors, vasodilators, demineralized bone or bone morphogenetic proteins; lipids; carbohydrates; proteoglycans; antiangiogenins; antigens; demineralised bone matrix (DBM); hyaluronic acid and salts and derivatives thereof; polysaccharides; cellulose compounds and derivatives thereof; antibodies; gene therapy reagents; genetically altered cells, stem cells including mesenchymal stem cells with transforming growth factor, and/or other cells; cell growth factors; type II collagen; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1); Lim Mineralization Protein-1 (LMP-1); cartilage; oxygen-containing components; enzymes; melatonin; vitamins; and nutrients.

In one embodiment the additive comprises aprotinin; and calcium ions. In another embodiment the implant comprises: an anti-inflammatory agent. Optionally, the anti-inflammatory agent comprises: inhibitors of a plurality of cytokines. Further optionally, the cytokines are selected from the group consisting of: interleukin 1 (IL-1), interleukin 6 (IL-6), interleukin 8 (IL-8), tumor necrosis factor-alpha (TNF-a), and metalloproteinases. Optionally, the anti-inflammatory agent is selected from the group consisting of: tumor necrosis factor antagonists; Interleukin antagonists; and anti-inflammatory nutraceuticals.

In one yet further embodiment the additive comprises growth factors. Optionally, the growth factors are selected from the group consisting of: transforming growth factors; insulin-like growth factors; platelet-derived growth factor; bone morphogenetic protein-2; bone morphogenetic protein-7; and growth/differentiation factor-5.

In one further embodiment, the implant further comprises an occlusion material arranged to substantially occlude an annual tear in conjunction with the support member sections, the proximal securing members and the inter-annulus support members. Optionally, the occlusion material comprises one of: super-absorbable particles embedded in fabric; and in-situ curing material.

Independently, certain embodiments provide for a method for production of an implant for repair of a spinal intervertebral disc, the method comprising: providing a first sheet of bio-compatible material and a second sheet of bio-compatible material; for each of the first sheet and the second sheet: cutting a support member section from the sheet, the support member section exhibiting a longitudinal axis, the support member section having a first face and a second face opposing the first face, the support member further having a distal end and a proximal end; cutting a proximal securing member from the sheet, the proximal securing members secured to the proximal end of the support member section and arranged to extend proximally thereof; cutting a pair of inter-annulus support members from the sheet, each of the pair of inter-annulus support members arranged on opposing sides of the longitudinal axis of the support member section along the proximal end, each of the pair of inter-annulus support members exhibiting a first end secured to the proximal end of the support member section, a second end and a link member coupling the first end to the second end, each of the inter-annulus support members cut in a deployed configuration wherein the second end of each of the inter-annulus support members extends away from the longitudinal axis of the axial support member section, a first face of each of the inter-annulus support members generally facing the support member section and generally concavingly curved when viewed from the proximal end of the support member section, and a second face of each of the inter-annulus support members generally convexingly curved when viewed from the proximal end of the support member section; shaping each proximal support member to the deployed configuration so as to distend in the direction of the first face of the support member section; and securing the support member section of the first sheet to the support member section of the second sheet such that the second face of the first sheet support member section faces the second face of the second sheet support member section.

In one further embodiment, each of the pair of inter-annulus support members comprises a plurality of stacked layers, each of the plurality of stacked layers exhibiting a first end secured to the proximal end of the support member section, a second end and a link member coupling the first end to the second end, wherein in the deployed configuration a first face of each of the inter-annulus support member layers generally faces the support member section and is generally concavingly curved when viewed from the proximal end of the support member section, and a second face of each of the inter-annulus support members is generally convexingly curved when viewed from the proximal end of the support member section. In one yet further embodiment, at least one of the plurality of stacked layers further comprising a protrusion at the second thereof arranged so as to arrest movement of an adjacent layer, at a predetermined point, caused by a force applied to the adjacent layer, the protrusion provided member and the adjacent layer layers thus cooperating under the force to act as a single layer.

Independently, certain embodiments provide for a method for repairing a spinal inter-vertebral disc, the method comprising: providing an implant comprising: a first section and a second section, each of the first section and the second section comprising: a support member section exhibiting a longitudinal axis, the support member section having a first face and a second face opposing the first face, the support member further having a distal end and a proximal end; a proximal securing member secured to the proximal end of the support member section and arranged to extend proximally thereof, the proximal securing member arranged in a deployed configuration to distend in the direction of the first face of the support member section; and a pair of inter-annulus support members, each of the pair of inter-annulus support members arranged on opposing sides of the longitudinal axis of the support member section along the proximal end, each of the pair of inter-annulus support members exhibiting a first end secured to the proximal end of the support member section, a second end and a link member coupling the first end to the second end, each of the inter-annulus support members having a deployed configuration wherein the second end of each of the inter-annulus support members extends away from the longitudinal axis of the axial support member section, a first face of each of the inter-annulus support member generally facing the support member section and generally concavingly curved when viewed from the proximal end of the support member section, and a second face of each of the inter-annulus support member generally convexingly curved when viewed from the proximal end of the support member section, the support member section of the first section secured to the support member section of the second section such that the second face of the first section faces the second face of the second section; delivering the provided implant into a target annulus; and moving the at least one inter-annulus support member into the deployed configuration, wherein in the deployed configuration the at least one inter-annulus support member is arranged to come in contact with an inner wall of the target annulus.

In one further embodiment, each of the pair of inter-annulus support members comprises a plurality of stacked layers, each of the plurality of stacked layers exhibiting a first end secured to the proximal end of the support member section, a second end and a link member coupling the first end to the second end, wherein in the deployed configuration a first face of each of the inter-annulus support member layers generally faces the support member section and is generally concavingly curved when viewed from the proximal end of the support member section, and a second face of each of the inter-annulus support members is generally convexingly curved when viewed from the proximal end of the support member section. In one yet further embodiment at least one of the plurality of stacked layers further comprising a protrusion at the second thereof arranged so as to arrest movement of an adjacent layer, at a predetermined point, caused by a force applied to the adjacent layer, the protrusion provided member and the adjacent layer layers thus cooperating under the force to act as a single layer.

Additional features and advantages of the invention will become apparent from the following drawings and description.

BRIEF DESCRIPTION OF THE DRAWINGS

For a better understanding of various embodiments of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 8 illustrates a high level flow chart of a method for providing an additive to any of the above implants;

DETAILED DESCRIPTION

Figure 1A:
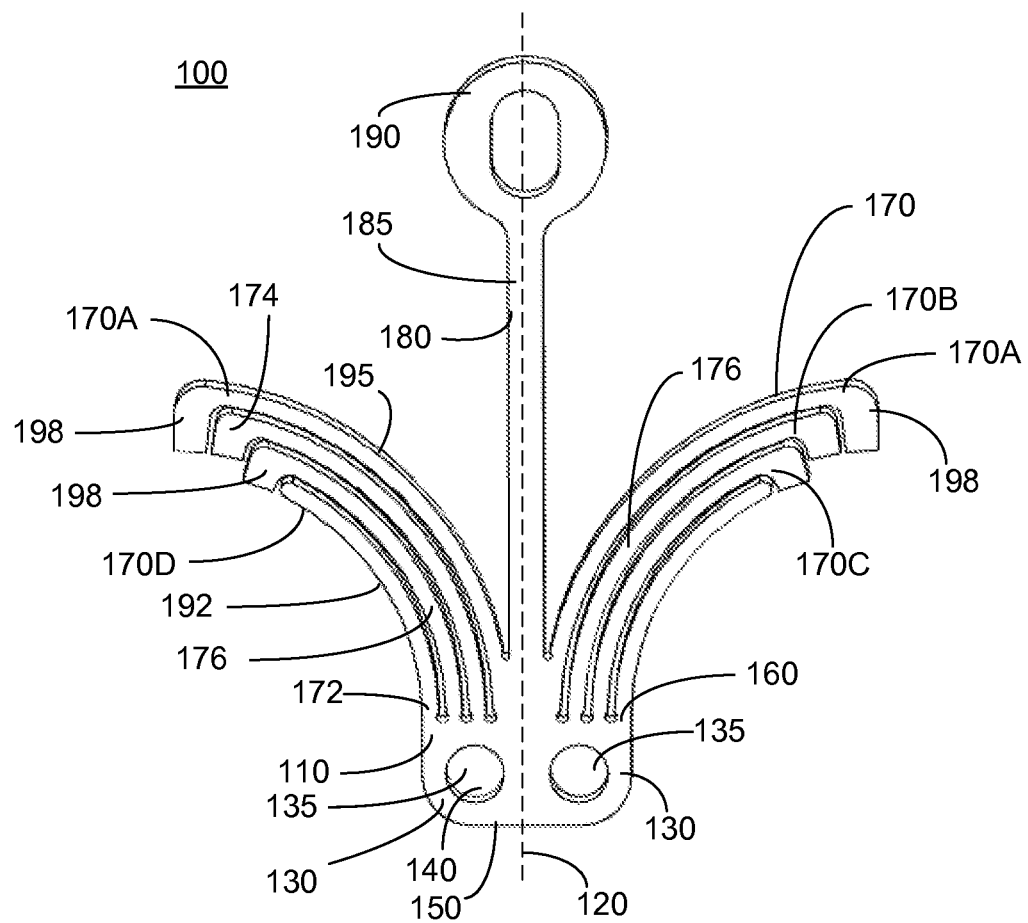
FIGS. 1A-1B illustrate a plurality of views of a single section of a first embodiment of an implant for repair of a spinal inter-vertebral disc, the section exhibiting a plurality of interlocking inter-annulus support members connected to a support member, and a unitary proximal securing member.

Before explaining at least one embodiment in detail, it is to be understood that the invention is not limited in its application to the details of construction and the arrangement of the components set forth in the following description or illustrated in the drawings. The invention is applicable to other embodiments being practiced or carried out in various ways. Also, it is to be understood that the phraseology and terminology employed herein is for the purpose of description and should not be regarded as limiting.

Figure 1B:
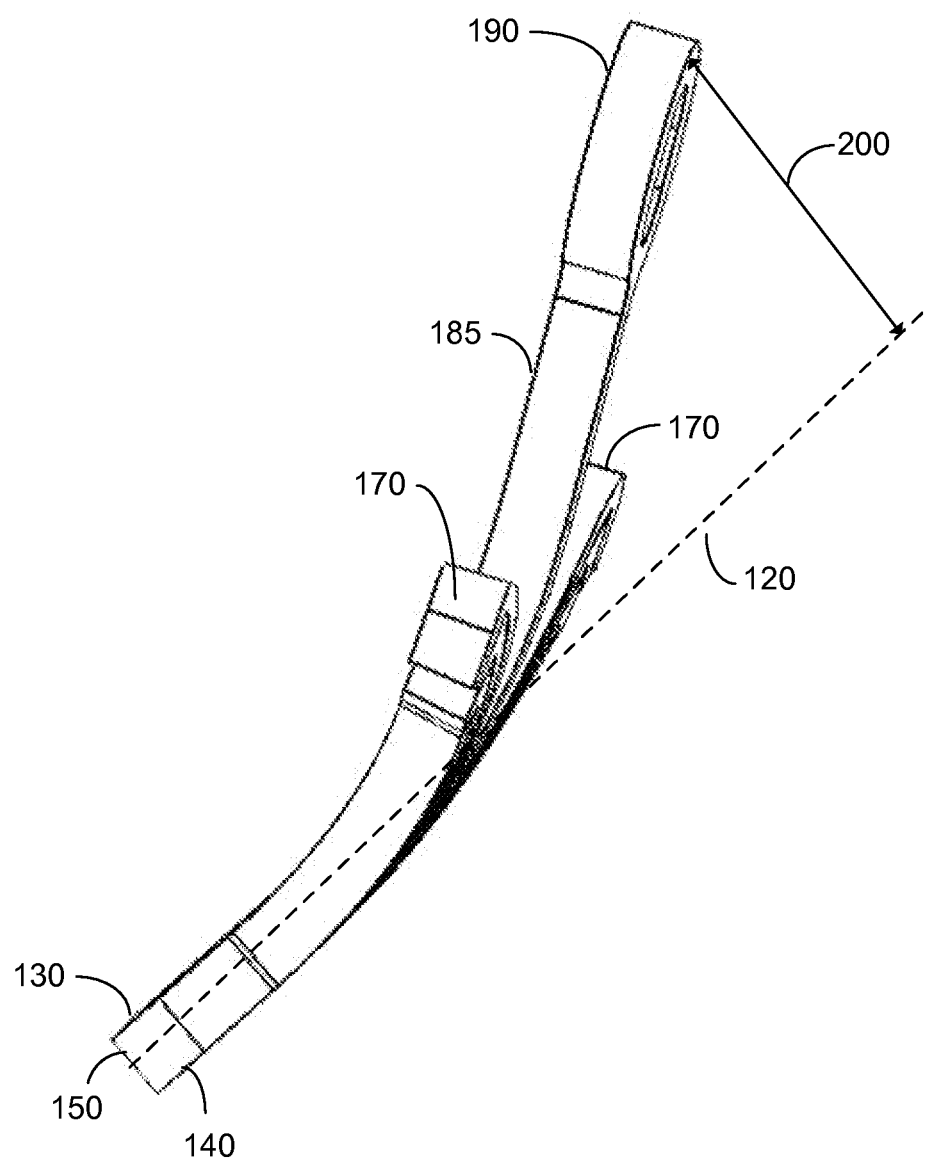

FIG. 1A illustrates a high level side view of a single section 100 of a first embodiment of an implant for repair of a spinal inter-vertebral disc; and FIG. 1B illustrates a perspective view of section 100 after shape setting to the deployed configuration. Section 100 comprises: a support member section 110 exhibiting a longitudinal axis 120, a first face 130, a second face 140 opposing first face 130, one or more holes 135 extending from first face 130 to second face 140, a distal end 150 and a proximal end 160; a plurality of inter-annulus support members 170 each exhibiting a plurality of layers 170A, 170B, 170C and 170D; and a proximal securing member 180. Layer 170A is adjacent layer 170B, layer 170B is adjacent layer 170C and layer 170C is adjacent layer 170D. Proximal securing member 180 comprises an extending member 185 and an extension member 190 which in one embodiment is shaped generally as a circle. In one embodiment, proximal securing member 180 is constituted of a unitary member. In one embodiment, section 100 is formed from a plate with a thickness such that the distance between first face 130 and second face 140 of support member section 110 is 0.1-2 mm, optionally about 0.8 mm. In one embodiment, section 100 is formed by laser-cutting a plate of shape memory alloy. In another embodiment, the distance between adjacent layers of the plurality of layers is 0-4 mm, optionally about 0.3 mm. In another embodiment, each of the plurality of stacked layers 170A, 170B, 170C and 170D exhibits a thickness of 0.05-0.5 mm, optionally about 0.25 mm.

Each layer of inter-annulus support members 170 exhibits: a first end 172 secured to proximal end 160 of support member section 110; a second end 174, opposing first end 172; a link member 176 connecting first end 172 with second end 174; a first face 192; and a second face 195, opposing first face 192. Each layer 170A, 170B and 170C forming the respective inter-annulus support member 170 further exhibits a protrusion 198 extending from second end 174 thereof and arranged to block the advancement of the adjacent layer when second end 174 of the adjacent layer comes in contact with protrusion 198 responsive to ejection forces, as will be explained further below, thus providing an increased strength, i.e. resistance to ejection forces, without requiring thick members.

First face 192 of layer 170A faces second face 195 of adjacent layer 170B, first face 192 of layer 170B faces second face 195 of adjacent layer 170C, first face 192 of layer 170C faces second face 195 of adjacent layer 170D and first face 192 of layer 170D generally faces support member section 110. Each inter-annulus support member 170 is illustrated as being formed by 4 layers, however this is not meant to be limiting in any way and any number of layers may be provided without exceeding the scope. The layers of each inter-annulus support member 170 are stacked along the edge of proximal end 160 proceeding out from longitudinal axis 120 in a respective direction. Thus a respective inter-annulus support member 170 is provided at each side of longitudinal axis 120. For ease of construction, in one embodiment each section 100 exhibits a matched pair of inter-annulus support members 170. Preferably, section 100 is cut from a single plate with inter-annulus support members 170 being cut into the curved state, as described above.

As shown in FIG. 1B, after cutting section 100 from a plate, such as by laser cutting, or forming section 100 from parts, section 100 is shaped to the desired deployed state. In an exemplary embodiment, section 100 is formed from a shape memory alloy, such as Nitinol. In the desired deployed state, the proximal end of extension member 190 is displaced from longitudinal axis 120 by distance 200, with extending member 185 generally curving in a convex curve away from longitudinal axis 120. In one embodiment, distance 200 is between 3.5 mm and 9 mm. It is to be noted that inter-annulus support members 170 generally curve parallel to the curve of extending member 185, however this is not meant to be limiting in any way. Inter-annulus support members 170, when cut from a single plate with proximal securing member 180, typically follow any bending performed on extending member 185 to achieve distance 200. Extension member 190 faces first face 130 and faces away from second face 140.

In the deployed configuration, first face 192 of each layer of inter-annulus support members 170 extends in a concave curve to second end 174 thereof when viewed from proximal end 160, and second face 195 extends in a convex curve to second end 174 thereof when viewed from proximal end 160. Proximal securing member 180 is illustrated as comprising a single layer, however this is not meant to be limiting in any way and any number of layers may be provided without exceeding the scope.

The use of layers allows for a device which is easily compacted to a delivery configuration, while cooperating to provide resistance to ejection forces, as will be described below in relation to FIGS. 3A-3B.

Figure 2A:
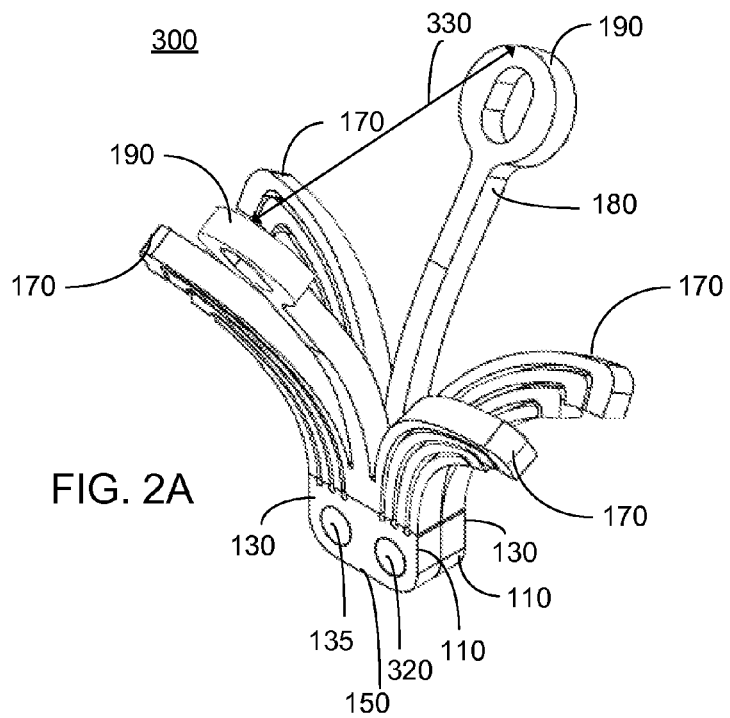
FIGS. 2A-2D illustrate a plurality of views of an implant for repair of a spinal inter-vertebral disc formed from a pair of single sections as described in relation to FIGS. 1A-1B.
Figure 2B:
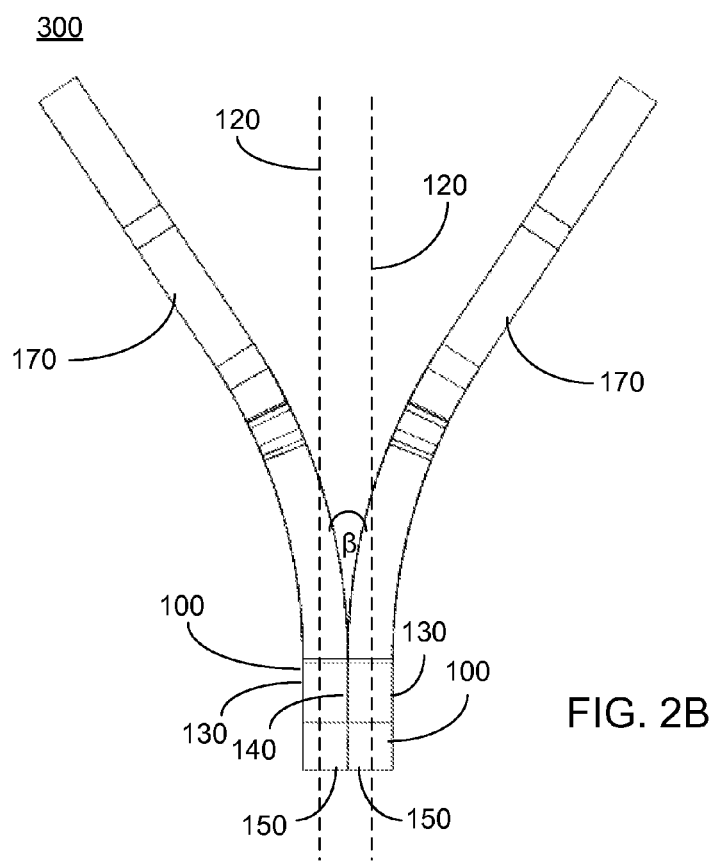
Figure 2C:
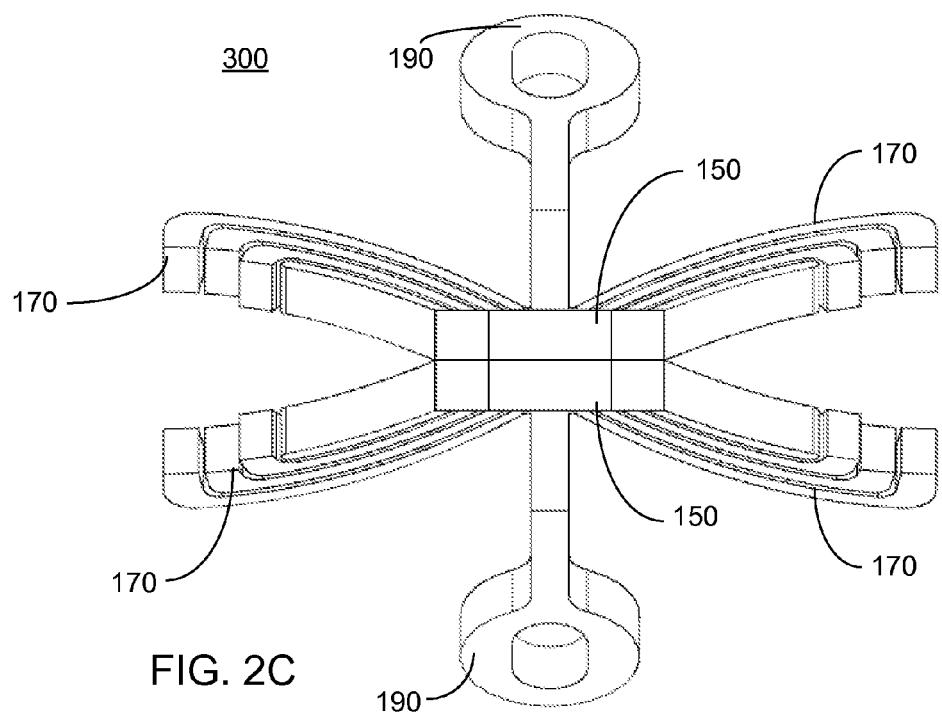
Figure 2D:
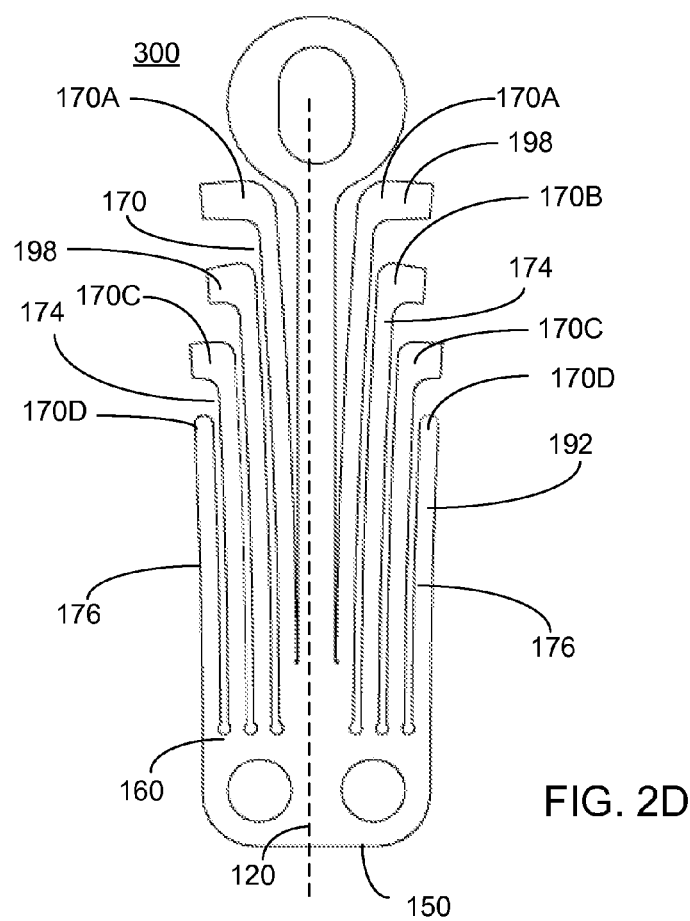

FIG. 2A illustrates a high level perspective view of an implant 300 for repair of a spinal inter-vertebral disc in a deployed configuration formed from a pair of sections 100 of FIGS. 1A-1B; FIG. 2B illustrates a high level side view of implant 300 in the deployed configuration; FIG. 2C illustrates a high level bottom view of implant 300 in the deployed configuration; and FIG. 2D illustrates a high level front view of implant 300 in the delivery configuration, the figures being described together. Implant 300 comprises: a first and a second section 100, each as described above, wherein face 140 of a first support member section 110 has been secured to face 140 of a second support member section 110 with distal ends 150 aligned. In one particular embodiment first and second support member section 110 are welded to each other.

In one embodiment, as described above, each support member section 110 further exhibits one or more holes 135 extending from first face 130 to second face 140, each hole 135 of first section 100 arranged to be aligned with a respective hole 135 of second section 100. A connection member 320 is optionally arranged to extend through each aligned pair of holes 135 thereby connecting first and second support member sections 110.

The layers of inter-annulus support member 170 of each section 100 are generally convexingly curved away from the respective longitudinal axis 120 as described above, and the combination forms an angle β between the inter-annulus support members 170 of first section 100 and the inter-annulus support members 170 of second section 100, as illustrated in FIG. 2B. As described further below, angle β causes the points of contact of each inter-annulus support member 170 with an inner wall of a target annulus to extend in the superior and inferior directions, i.e. in the directions of adjacent vertebrae. In one embodiment, medical material is deposited within the target disc and implant 300 is arranged to prevent the extrusion of the deposited medical material therefrom.

The distance between the proximal ends of the respective extension members 190, shown as distance 330, is twice distance 200 described above, plus ½ the thickness of the respective support member sections 110. Distance 330 is optionally between 6-15 mm, and in one particular embodiment is about 9 mm.

As shown in FIG. 2D, implant 300 is crimped to a delivery configuration. In one embodiment, in the delivery configuration implant 300 exhibits a profile of 0.4 mm to 3 mm in thickness with a 2-9 mm width. In one particular embodiment, in the delivery configuration implant 300 exhibits a profile of 1.6 mm×4 mm. In general, in the delivery configuration, inter-annulus support members 170 are constrained to lie within the plane defined by the outer dimensions of support member section 110. Advantageously, layers 170A-170D are not constrained by protrusions 198 from moving to the delivery configuration, and thus thinner layers which are more compliant for movement to and from the delivery configuration may be utilized. As described below, the thinner layers provide mutual support under force responsive to protrusions 198.

Figure 3A:
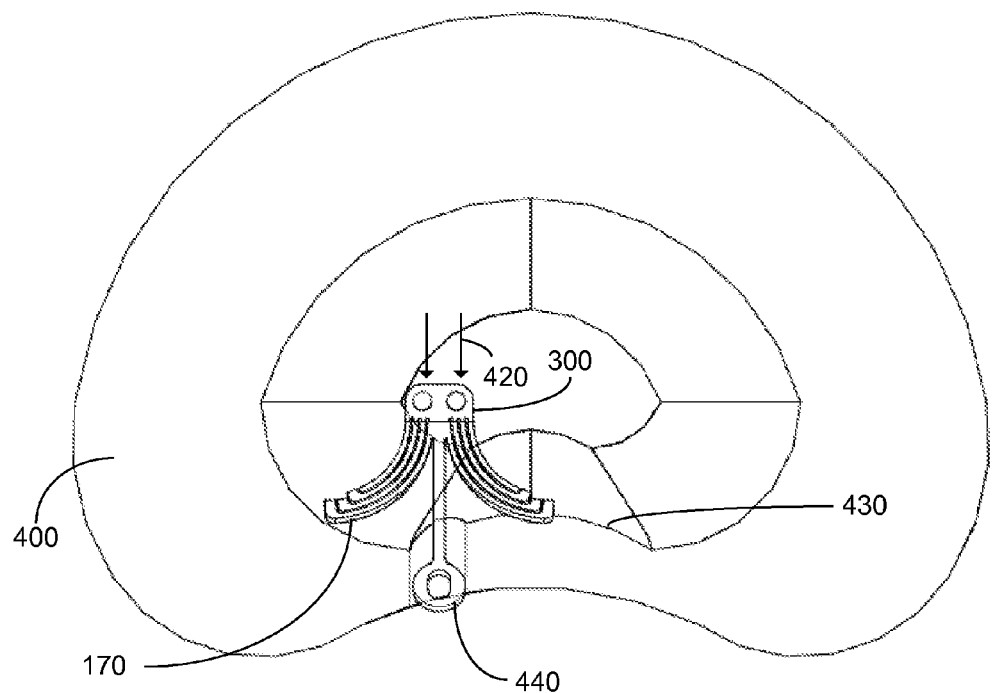
FIGS. 3A-3B illustrate a plurality of views of the implant of FIGS. 2A-2D deployed within a target annulus.
Figure 3B:
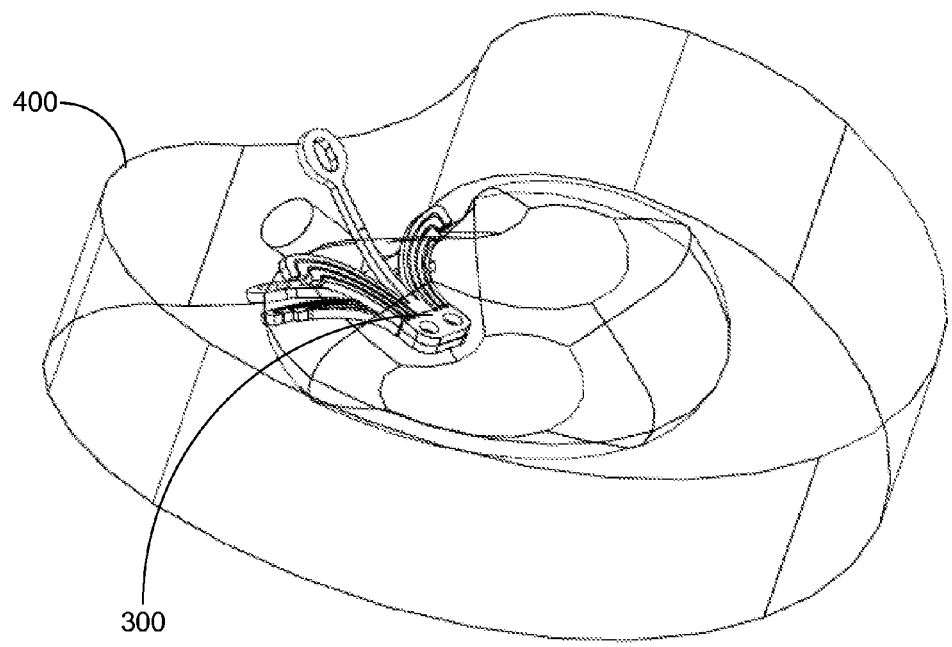

FIG. 3A illustrates a high level top view of implant 300 deployed within a target annulus 400, and FIG. 3B illustrates a perspective view of implant 300 deployed within target annulus 400, particularly within a channel 440 with ejection forces experienced by implant 300 illustrated by arrows 420, and denoted ejection force 420.

When ejection force 420 is applied to implant 300 inter-annulus support members 170 are pushed into contact with inner wall 430 of target annulus 400. Layer 170D deforms responsive to ejection force 420 and extends to contact protrusion 198 of layer 170C thus adding the strength of layer 170C to resist ejection force 420. Similarly, layer 170C deforms responsive to ejection force 420 and extends to contact protrusion 198 of layer 170B thus adding the strength of layer 170B to resist ejection force 420. Similarly, layer 170B deforms responsive to ejection force 420 and extends to contact protrusion 198 of layer 170A thus adding the strength of layer 170A to resist ejection force 420. The advancement of each layer is thus blocked by protrusion 198 of the adjacent layer and the layers cooperate together to act as a single layer.

In particular, the deflection of each inter-annulus support member 170 decreases by a cubic function of the added thickness of inter-annulus support member 170. The layer arrangement of inter-annulus support member 170 forms a leaf spring type arrangement and thus provides for improved resistance to ejection force 420 while allowing for a more compliant single layer. The stiffness of a leaf spring is given as:

$$k=(E*n*b*t^3)/(6*L^3) \qquad \text{EQ.1}$$

where 'E' is Young's modulus of the leaves, 'n' is the number of leaves, 'b' is the width of the leaves, 't' is the thickness of the leaves and 'L' is the length of the leaves. As can be seen by EQ. 1, the more leaves in the spring the greater the stiffness. Thus, the use of multiple layers achieves an increased resistance to ejection responsive to ejection force 420, while allowing for the use of a thinner, more compliant material per layer to aid in movement from the deployed configuration to the delivery configuration without excessive stresses and cracking.

In one embodiment, second face 195 of each inter-annulus support member layer 170A comes in contact with inner wall 430 of annulus 400 at a distance of 1-12 mm from the edge of channel 440. Advantageously, this provides for contact of inter-annulus support members 170 with healthier tissue thus avoiding damage to the wall of annulus 400 in the vicinity of channel 440, which as described above is in the vicinity of a tear. Additionally, due to the shape of inter-annulus support member layers 170, which as described above is in one embodiment concave, responsive to ejection force 420 applied to implant 300 inter-annulus support member layers 170 extend further along inner wall 430 of annulus 400 thereby further distancing themselves from channel 440 and applying pressure to a more healthier portion of annulus 400.

Friction between proximal securing members 180 and the inner wall of channel 440 prevents movement of implant 300, particularly responsive to forces applied thereto in directions which differ from the direction of ejection force 420.

In one embodiment, the size of circle shaped extension member 190 is arranged such that when implant 300 is positioned within target annulus 400, extension member 190 exhibits friction with the inner walls of a tear, or opening, of target annulus 400. In another embodiment, the length of extending member 185 is arranged such that when implant 300 is positioned within target annulus 400, extension member 190 exhibits friction with the outer walls of target annulus 400. In another embodiment, extension member 190 is sized and shaped so as to provide friction with the inner walls of target annulus 400, the outer walls of target annulus 400 and the inner walls of the tear, or opening of target annulus 400. In another embodiment, extension member 190 is not circle shaped and is sized and shaped to provide friction, as described above.

As described above, in one embodiment, implant 300 is manufactured from a pair of single plates, and cut into the deployed configuration, thus avoiding the creation of micro-cracks which may occur in the event that implant 300 was formed in the delivery configuration illustrated in FIG. 2D. Such micro-cracks are advantageously avoided, since when ejection force 420 is applied to implant 300, as described above, the micro-cracks can cause inter-annulus support members 170 to break. Advantageously, when inter-annulus support members 170 are created in the deployed configuration only a minimal shape setting process in the sagittal direction is necessary and therefore excessive stresses and micro-cracks during shape setting process are avoided.

Figure 4A:
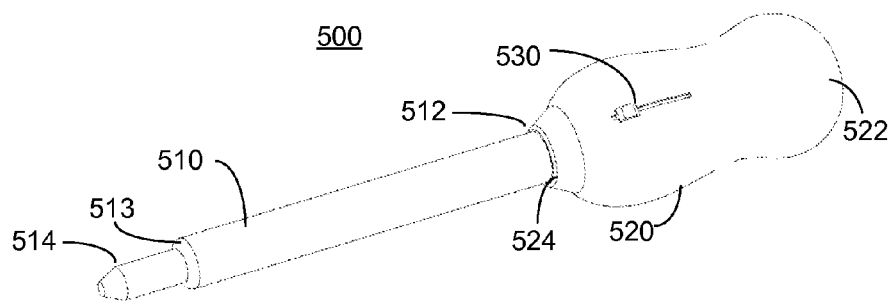
FIG. 4A illustrates a perspective view of a delivery system for delivering an implant into a target annulus.
Figure 4B:
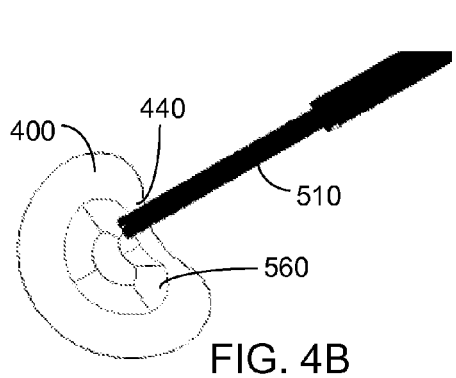
FIGS. 4B-4D illustrate various stages in the deployment of an implant into the target annulus.
Figure 4C:
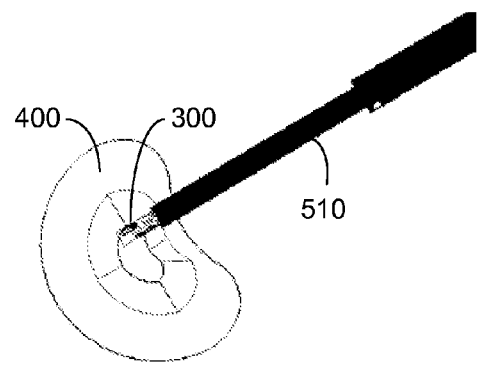
Figure 4D:
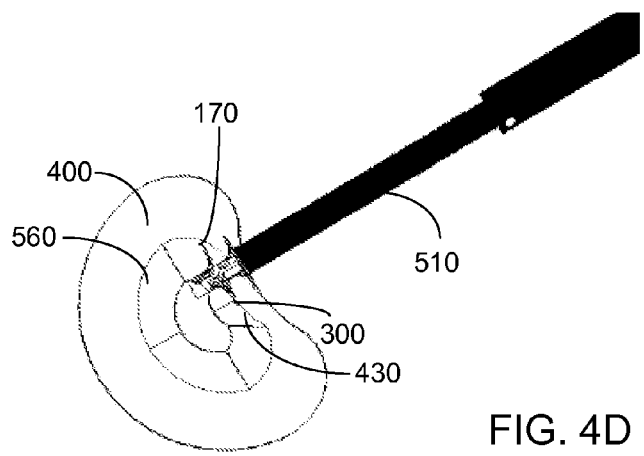

FIG. 4A illustrates a perspective view of a delivery system 500 for delivering implant 300 into annulus 400, FIG. 4B illustrates a perspective view of delivery system 500 with a distal end thereof inserted through channel 440 into area 560 of annulus 400, FIG. 4C illustrates a perspective view of a partial deployment of implant 300 into annulus 400 and FIG. 4D illustrates a perspective view of full deployment of implant 300 into annulus 400. For ease of understanding, FIGS. 4A-4D will be described together. Delivery system 500 comprises: a restraining device, such as a delivery tube 510, exhibiting a proximal end 512 and a distal end 514; a handle 520, exhibiting a proximal end 522 and a distal end 524; and a delivery lever 530. In one embodiment, distal end 514 of delivery tube 510, beginning distally of a ridge 513, is narrower than the rest of delivery tube 510, thereby allowing entry of distal end 514 of delivery tube 510 into channel 440, while allowing for a thicker proximal portion of delivery tube 510 for mechanical stability. Proximal end 512 of delivery tube 510 is connected to distal end 524 of handle 520. In one embodiment, an extension of delivery lever 530 is slideably secured to the side of handle 520 and is arranged to push implant 300 which is situated within delivery tube 510. In another embodiment (not shown), an extension of delivery lever 530 is attached to proximal end 522 of handle 520.

Implant 300 is situated inside delivery tube 510 in the delivery configuration, as described above. A channel 440 of annulus 400 is a result of pathology and/or surgical expansion of an existing tear. Delivery tube 510 is inserted into channel 440, as illustrated in FIG. 4B. Advantageously, the diameter of ridge 513 is greater than the diameter of channel 440 thereby contact of ridge 513 with the outer walls of annulus 400 provides an indication to the user to cease advancement of delivery tube 510, and further prevents deployment of implant 300 at an inappropriate depth within annulus 400. Delivery lever 530 is advanced, optionally by turning handle 520. As delivery lever 530 advances, it pushes implant 300 out of delivery tube 510, as illustrated in FIG. 4C. As second end 174 of each of plurality of inter-annulus support members 170 exits delivery tube 510, plurality of inter-annulus support members 170 are urged to move from the delivery configuration to the deployed configuration. In one embodiment, inter-annulus support members 170 are elastically forced into the delivery configuration and inherently urge to return to the deployed configuration. In another embodiment, inter-annulus support members 170 urge to the deployed configuration responsive to body heat.

Plurality of inter-annulus support members 170 secure implant 300 against inner wall 430 of annulus 400 as described above. Delivery tube 510 is withdrawn from channel 440 and withdrawn from over the remainder of implant 300, exposing plurality of proximal securing members 180 (not shown). Proximal securing members 180 move to the deployed configuration and secure implant 300 to the outer walls of annulus 400, or to the inner walls of channel 440. In one embodiment, proximal securing members 180 are elastically forced into the delivery configuration and inherently urge to return to the deployed configuration. In another embodiment, proximal securing members 180 urge to the deployed configuration responsive to body heat.

Figure 5A:
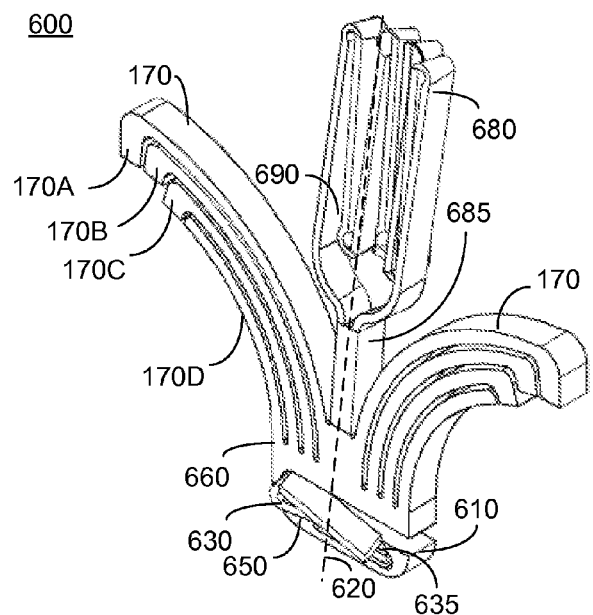
FIGS. 5A-5B illustrate a plurality of views of a single section of a second embodiment of an implant for repair of a spinal inter-vertebral disc, the section exhibiting a plurality of interlocking inter-annulus support members connected to a support member having an elastic portion, and a proximal securing member having an extending portion.
Figure 5B:
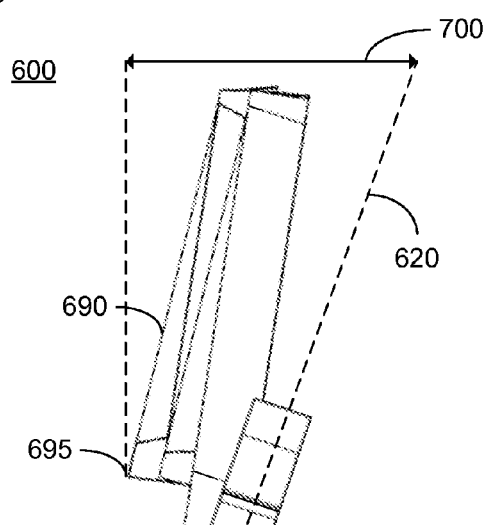

FIG. 5A illustrates a high level perspective view of a single section 600 of a second embodiment of an implant for repair of a spinal inter-vertebral disc; and FIG. 5B illustrates a perspective view of section 600 after shape setting to the deployed configuration, the drawings being described together. Section 600 is similar to section 100, except as described below, and comprises: a support member section 610 exhibiting a longitudinal axis 620, a first face 630, a second face 640 opposing first side 630, an elastic member 635, a distal end 650 and a proximal end 660; a plurality of inter-annulus support members 170 each exhibiting a plurality of layers 170A, 170B, 170C and 170D; and a proximal securing member 680 having an extending portion 690. Layers 170A-170D are substantially as described above in relation to section 100 and thus are not further described. Proximal securing member 680 comprises an extending member 685 and an extension portion 690 which in one embodiment is shaped generally in a serpentine configuration. In one embodiment, proximal securing member 680 is constituted of a unitary member. In one embodiment, section 600 is formed from a plate with a thickness such that the distance between first face 630 and second face 640 of support member section 610 is 0.2-2 mm. In one embodiment section 600 is formed by laser-cutting a plate of shape memory alloy.

As shown in FIG. 5B, after cutting section 600 from a plate, such as by laser cutting, or forming section 600 from parts, section 600 is shaped to the desired deployed state. In an exemplary embodiment, section 600 is formed from a shape memory alloy, such as Nitinol. In the desired deployed state, extending portion 690 is distended into a staircase type configuration so as to provide a partially filled expansion between a maximal extension point 695 of each extending portion 690 and longitudinal axis 620, as illustrated by distance 700, without excessive deformation of the material of extending portion 690 yet providing increased coverage in the Sagittal plane for the prevention of ejection of nucleus pulposus material. Each strut of extending portion 690 increases the coverage area in the Sagittal plane. There is no requirement that maximal extension point 695 occur at the ultimate proximal end of extending portion 690, and the maximal distance 700 may be exhibited at the ultimate proximal end of extension portion 690, or partway between the ultimate proximal and distal ends without exceeding the scope. In an exemplary embodiment, extending portion 690 cooperates with inter-annulus support member 170 and support member section 610 to occlude 20%-95% of a target channel 440. In one embodiment, distance 700 is between 3.5 mm and 9 mm, similar to distance 200, however increased area coverage is provided.

Extending portion 690 is illustrated as formed in a staircase type configuration, however this is not meant to be limiting in any way, and other forms such as a spiral extending portion may be provided without exceeding the scope.

Elastic member 635 is similarly distended to extend away from longitudinal axis 620 in the direction of second face 640, such that a far face 637 of elastic member 635 extends away from second face 640 by a distance 710.

In one embodiment, as illustrated, inter-annulus support members 170 are in a plane with longitudinal axis 620, and in another embodiment inter-annulus support members 170 are curved convexingly as described above in relation to inter-annulus support members 170 of section 100.

Figure 6A:
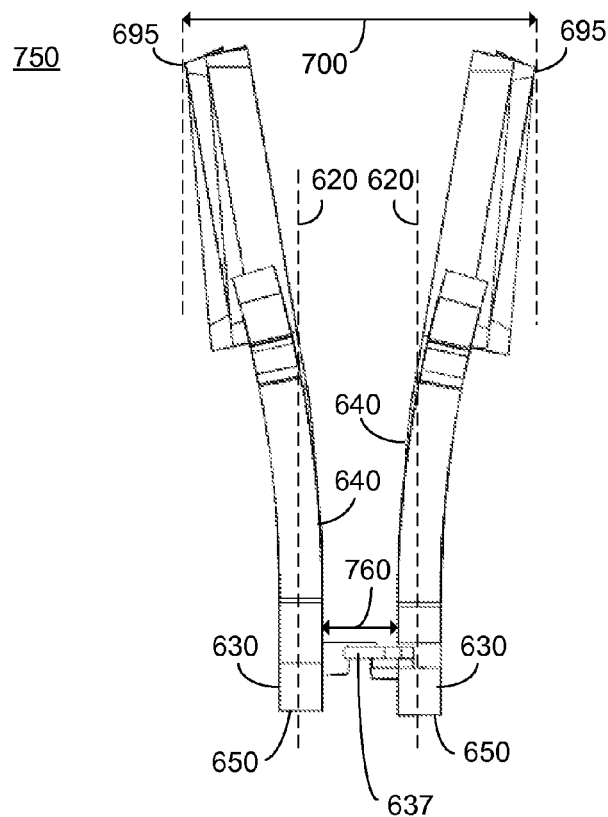
FIG. 6A illustrates a side view of an implant for repair of a spinal inter-vertebral disc formed from a pair of single sections as described in relation to FIGS. 5A-5B.
Figure 6B:
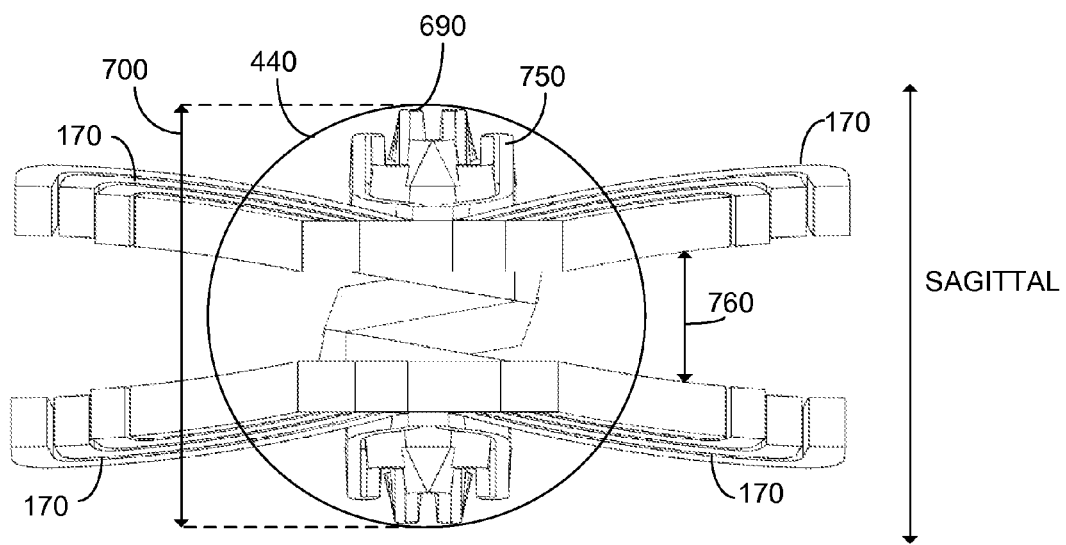
FIG. 6B illustrates a high level top view of the implant of FIG. 6A in the deployed configuration.

FIG. 6A illustrates a high level side view of an implant 750 for repair of a spinal inter-vertebral disc in a deployed configuration formed from a pair of sections 600 of FIGS. 5A-5B; and FIG. 6B illustrates a high level bottom view of implant 750 in the deployed configuration within channel 440 of a target annulus as described above, the figures being described together for ease of understanding. Implant 750 comprises: a first and a second section 600, each as described above, wherein second face 640 of a first support member section 610 faces second face 640 of a second support member section 610 with distal ends 650 aligned. In particular, far face 637 of elastic portion 635 of first support member section 610 is secured to far face 637 of elastic portion 635 of second support member section 610, where far face 637 is maximally removed from second face 640 of the respective support member section. In one non-limiting embodiment the respective far faces 637 are secured to each other by welding, thus defining a distance 760 between the respective second faces 640. Distance 760 is twice that of distance 710.

Advantageously, inter-annulus support members 170 of first section 600 are thus at a predetermined minimum distance 760 from inter-annulus support members 170 of second section 600 without requiring shaping, although as mentioned above shaping of inter-annulus support members 170 may also be performed without exceeding the scope.

Advantageously, elastic members 635, when secured together, form a spring-like mechanism, arranged to allow for flex and extension in the Sagittal plane without fatigue failure. After relaxation of any flex or extension motion in the Sagittal plane, responsive to elastic members 635, implant 750 returns to its original implanted shape. Ejection forces are resisted by inter-annulus support members 170 as described above. Channel 440 is illustrated as circular, however this is not meant to be limiting in any way. About 20%-95% of channel 440 is occluded by implant 750 responsive to the space occupied by elastic members 635, inter-annulus support members 170 and extending portions 690. Elastic members 635 are illustrated as a serpentine shape, however this is not meant to be limiting in any way, and a spiral, or staircase type shape may be utilized without exceeding the scope.

Insertion of implant 750 is in all respects identical to that of implant 300 and the interest of brevity will not be further detailed.

The above has been described in an embodiment wherein each support member section 610 comprises an elastic member 635, such that distance 760 is equal to twice distance 710, however this is not meant to be limiting in any way. In another embodiment only one support member section 610 comprises an elastic member 635, which defines distance 760. In such an embodiment, the support member section 610 not exhibiting elastic member 635 exhibits a connection point for securing far face 637 of elastic member 635 thereto.

Figure 7:
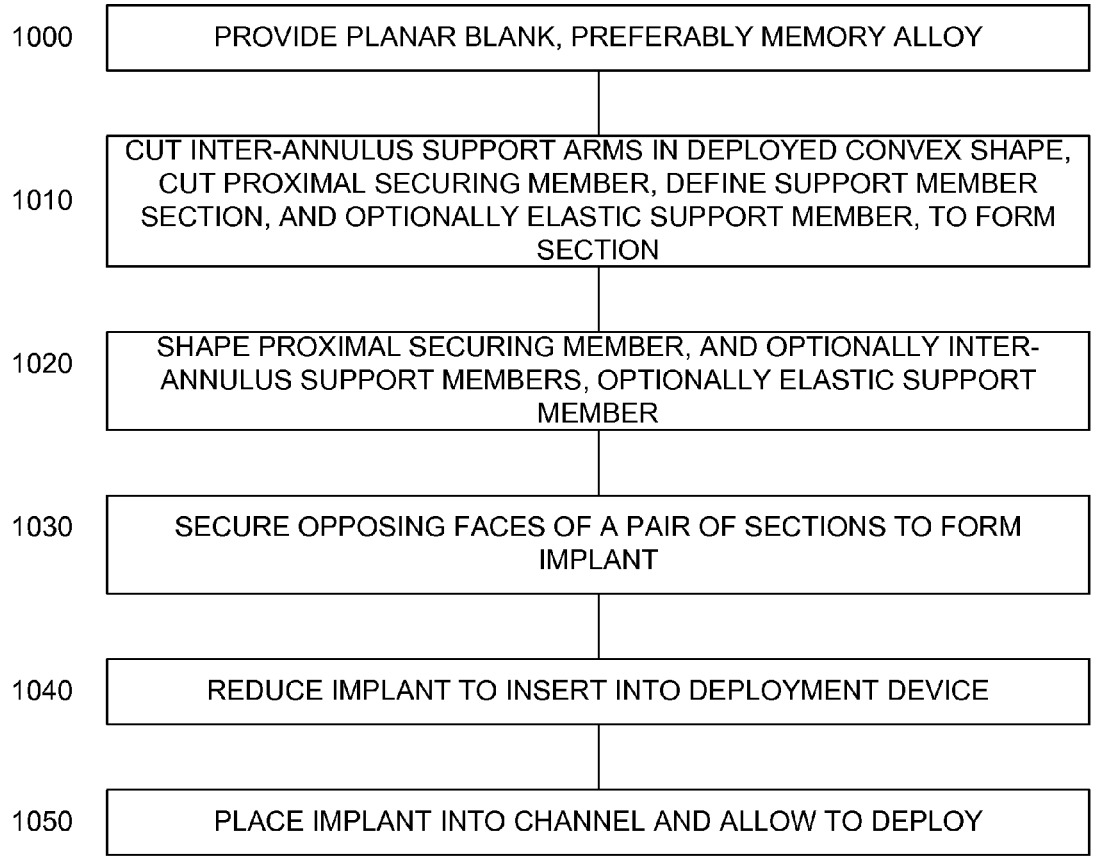
FIG. 7 illustrates a high level flow chart of a method for production of the implants of FIGS. 2A-2D and 6A-6B.

FIG. 7 illustrates a high level flow chart of a method for production of any of implants 300, 750 as described above. In stage 1000, a blank is provided, preferably of a memory alloy. In one embodiment the blank is a planar blank. In another embodiment, the blank is constituted of bio-compatible, bio-degradable, or bio-resorbable material. In one embodiment, the blank is constituted of a polymer and/or stainless steel. In another embodiment, the blank is constituted of Nitinol.

In stage 1010, inter-annulus support arms are cut from the provided blank in a deployed convex shape, as described above in relation to inter-annulus support arms 170. A proximal securing member, a support member, optionally an elastic support member, are each further defined and cut out from the provided blank, to form a section, as described above in relation to sections 100, 600.

In stage 1020, the proximal securing member of stage 1010 is shaped, as described above in relation to proximal securing members 180, 680. Optionally, inter-annulus support members are further to shaped to generally follow the extended shape of the respective proximal securing member. Optionally, the elastic support member is further shaped as described above in relation to elastic support member 635.

In stage 1030 opposing faces of a pair of sections defined in stages 1000-1020 are secured to each other to form an implant, as described above in relation to implants 300, 750. In stage 1040 the formed implant is reduced to a delivery configuration, by crimping the parts of the implant, and inserted into a deployment device. In stage 1050, the reduced implant is inserted into a pathological or surgical formed channel and allowed to deploy, thus providing a closure device for the spinal annulus.

FIG. 8 illustrates a high level flow chart of a method for providing an additive to any of implants 300, 750. In stage 2000, an additive is added to the particular implant. In one embodiment, the adding of the additive comprises: impregnating or coating at least a portion of the implant with the additive. In another embodiment, the adding of the additive comprises: coupling the additive to a portion of the implant. In another embodiment, a portion of the implant is designed to carry and deliver the additive to adjacent tissue.

In one embodiment, the additive is added to at least a portion of any of: inter-annulus support member layers 170A; 170B; 170C; and 170D and/or to proximal securing member 180, 680.

In optional stage 2010, the additive comprises a diagnostic agent. In one embodiment, the diagnostic agent comprises a radio-opaque material suitable to permit imaging by x-ray or magnetic resonance imaging (MRI).

In optional stage 2020, the additive comprises one or more therapeutic agents. In one embodiment, the therapeutic agent is selected from the group consisting of: antibiotics; antiproliferative, cytotoxic, and antitumor drugs including chemotherapeutic drugs; analgesic; antiangiogen; antibody; antivirals; cytokines; colony stimulating factors; proteins; chemoattractants; ethylenediaminetetraacetic acid (EDTA); histamine; antihistamine; erythropoietin; antifungals; antiparasitic agents; non-corticosteroid anti-inflammatory agents; anticoagulants; anesthetics; analgesics; oncology agents; cardiovascular drugs; vitamins and other nutritional supplements; hormones; glycoproteins; fibronectin; peptides including polypeptides and proteins; interferons; cartilage inducing factors; protease inhibitors; vasoconstrictors, vasodilators, demineralized bone or bone morphogenetic proteins; lipids; carbohydrates; proteoglycans; antiangiogenins; antigens; demineralised bone matrix (DBM); hyaluronic acid and salts and derivatives thereof; polysaccharides; cellulose compounds and derivatives thereof; antibodies; gene therapy reagents; genetically altered cells, stem cells including mesenchymal stem cells with transforming growth factor, and/or other cells; cell growth factors; type II collagen; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1); Lim Mineralization Protein-1 (LMP-1); cartilage; oxygen-containing components; enzymes; melatonin; vitamins; and nutrients.

In optional stage 2030, the additive comprises aprotinin and calcium ions. In optional stage 2040, the additive comprises an anti-inflammatory agent. In one embodiment, the anti-inflammatory agent comprises: inhibitors of a plurality of cytokines. In one further embodiment, the cytokines are selected from the group consisting of: interleukin 1 (IL-1), interleukin 6 (IL-6), interleukin 8 (IL-8), tumor necrosis factor-alpha (TNF-a), and metalloproteinases. In another embodiment, the anti-inflammatory agent is selected from the group consisting of: tumor necrosis factor (TNF) antagonists, such as Etanercept commercially available, under the trade name of Enbrel, from Amgen, Inc. of Thousand Oaks, Calif., or Infliximab commercially available, under the trade name Remicade, from Janssen Biotech, Inc. of Horsham, Pa.; Interleukin antagonists, such as Anakinra commercially available, under the trade name Kineret, from Amgen, Inc. of Thousand Oaks, Calif.; and anti-inflammatory nutraceuticals, such as glucosamine.

In optional stage 2050, the additive comprises growth factors. In one embodiment, the growth factors are selected from the group consisting of: transforming growth factors; insulin-like growth factors; platelet-derived growth factors; bone morphogenetic protein-2 (BMP-2); bone morphogenetic protein-7 (BMP-7); and growth/differentiation factor-5 (GDF5).

Figure 9:
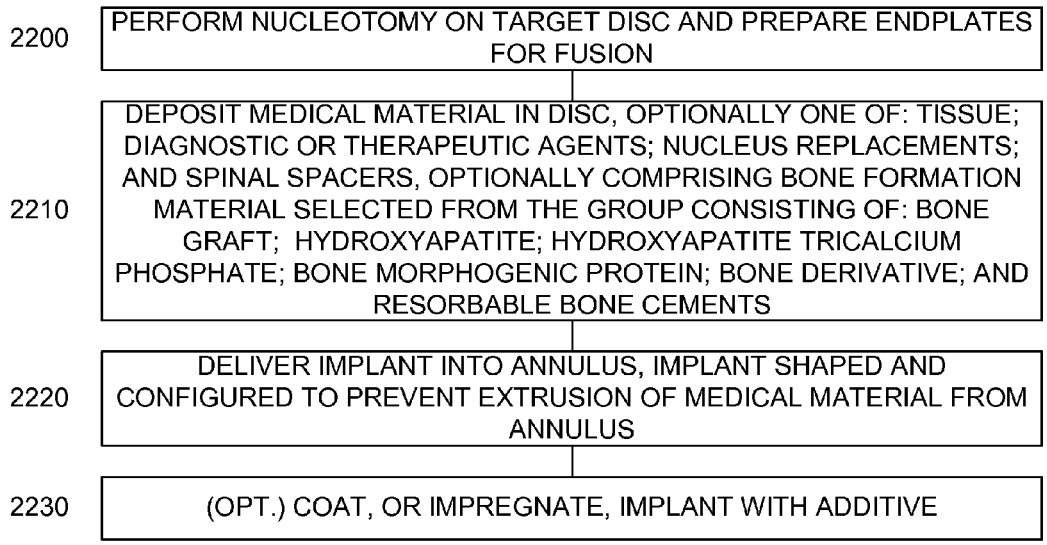
FIG. 9 illustrates a high level flow chart of a method for providing spinal fusion utilizing any of the above implants.

FIG. 9 illustrates a high level flow chart of a method for providing spinal fusion utilizing any of implants 300, 750. Spinal fusion is a surgical technique used to join two or more vertebrae utilizing bone graft placed between the vertebrae. Typically, screws and rods are placed in the spine and are used to keep bones from moving as the bone graft allows the stabilized bones to form a connection across a previously mobile disc space. Initially, fusion of the vertebral bones is done by laying bone graft between the bones to provide a scaffolding thereacross over which the native bone cells can grow. As the patient's bone cells move across the bone graft, the bone graft is incorporated into the patient's own bone structure thereby forming a complete connection.

Bone graft is advantageous in allowing the vertebral bones to fuse across a previously mobile segment. Studies of patient's with fusions done with bone graft alone have shown a relatively good rate of incorporation when patients are placed in back braces for 3 months or more. Because of the inconvenience and discomfort of the bracing, pedicle screws and rods have been added to provide an internal support that obviates the need for external supports. Internal screws and rods have increased successful fusion rates, as well as allowed patients to become mobile very quickly after the spinal fusion. Growth factors, such as bone morphogenetic proteins (BMPs) are utilized to induce bone formation but are difficult to localize, and subsequent diffusion from the site of interest and short half-life reduce the efficacy of the protein. Currently, spine fusion requires stripping, decortications of the transverse processes, and an autograft harvest procedure. Even in combination with BMPs, clinical spinal fusion has a high failure rate, presumably because of difficulties in localizing sufficient levels of BMP.

In stage 2200, nucleotomy is performed, as known in the prior art, to remove nucleus pulposus from the target disc and the adjacent endplates are prepared for fusion by minimally invasive means, as known in the prior art. In stage 2210, medical material is deposited into the target disc. In one embodiment, the medical material comprises bone formation material which exhibits: an osteogenic potential capable of directly providing cells to the newly forming bone; osteoinductive factors that can cause osteoprogenitor stem cells to differentiate into osteoblasts; and an osteoconductive scaffold that facilitates neovascularization and supports the ingrowth of bone. In one further embodiment, the bone formation material comprises one or more of: bone graft, for example HEALOS FX injectable bone graft, commercially available from DePuy Spine, Inc. of Raynham, Mass.; agents which cause fusing of vertebral bodies without a fusion rod by providing osteogenesis, osteoconduction, and/or osteoinduction; and any other natural or artificial material which encourages bone fusion. In one further embodiment, the bone formation material comprises morselized cortical, cancellous, or cortico-cancellous bone graft. In another further embodiment, the bone formation material comprises one or more of: an autograft; an allograft; allograft-based material, including demineralized bone matrix (DBM); cell-based gene therapy; and a xenograft. In another embodiment, the bone formation material comprises one or more of: a bone graft substitute; a combination of bone graft substitutes; and bone inducing substances. In one non-limiting embodiment, the bone formation material is selected from the group consisting of: hydroxyapatite; hydroxyapatite tricalcium phosphate; bone morphogenic protein (BMP); calcified or decalcified bone derivative; and resorbable bone cements. In one embodiment, the resorbable bone cement comprises one or more of: a calcium derivative generally composed of hydroxyapatite, orthophosphoric acid, calcium carbonate and calcium hydroxide formed into a semi-liquid paste with an alkaline solution of sodium hydroxide and water; a composition comprising polypropylene fumarate; a mixture of calcium phosphates; a calcium salt filler; N-vinyl-2-pyrrolidone; and a peroxide or free radical initiator. In one embodiment, the bone formation material is mixed with a radiographic material to enable its visualization during delivery so as to assure proper disposition and filling of bores, cavities and spaces within the target disc.

In another embodiment, the medical material comprises one or more of: tissue, such as morselized bone/nucleus pulposus; diagnostic agents; therapeutic agents; and mechanical devices, such as nucleus replacements and spinal spacers.

In stage 2220, an implant is delivered into a tear of the target annulus in a delivery configuration, as described above. In one embodiment, any of implants 300, 750 may be delivered in the target annulus. The delivered implant is shaped and configured to prevent the extrusion of the deposited medical material of stage 2210 through a tear in the target annulus as described above to prevent extrusion of the deposited medical material through the tear in the target annulus. Thus, the target disc remains filled with the deposited medical material of stage 2210 during fusion of the adjacent vertebrae. In optional stage 2230, the implant of stage 2220 is further coated or impregnated with an additive, as described above.

Figure 10:
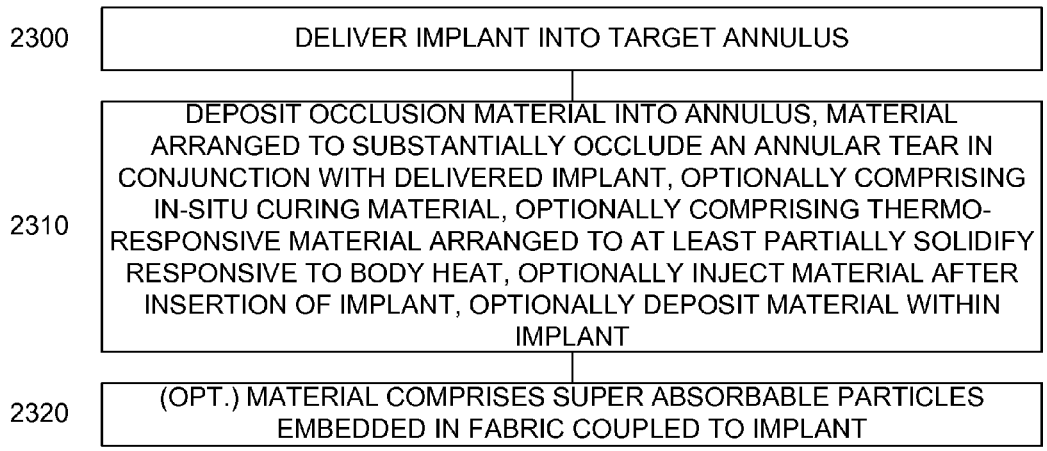
FIG. 10 illustrates a high level flow chart of a method of occluding an annulus tear utilizing any of the above implants.

FIG. 10 illustrates a high level flow chart of a method of occluding an annulus tear. In stage 2300, an implant is delivered into a target annulus, as described above in relation to implants 300, 750. In stage 2310, occlusion material is deposited into the target annulus. The deposited occlusion material is arranged to substantially occlude a tear in the target annulus in conjunction with the delivered implant. In particular, the delivered implant is arranged to act as a scaffold for the deposited occlusion material such that ejection forces don't eject the occlusion material from the target annulus. Optionally, the occlusion material comprises in-situ curing material, i.e. material that at least partially solidifies after injection into the target, such as silicon, fibrin glue, or cyanoacrylate. In one embodiment, the in-situ curing material comprises a thermo-responsive material arranged to at least partially solidify responsive to body heat. In another embodiment, the in-situ curing material is liquid and solidifies into a gel like form or a solid form. As the occlusion material solidifies the tear in the annulus is occluded thereby nucleus pulposus, or other material deposited within the disc, cannot exit the annulus. In one embodiment, the material is arranged to conform to the shape of the tear and provide complete occlusion thereof. As described above, ejection forces are normally applied towards the annulus tear and to any occlusion material near or in the tear. The occlusion material is arranged to solidify around and through the delivered implant of stage 2300, thereby the ejection forces are not able to eject the occlusion material from the annulus.

In one embodiment, the occlusion material is injected into the target annulus after the implant delivery of stage 2300. In another embodiment, the occlusion material is injected into the target annulus before the implant delivery of stage 2300 and the implant delivery of stage 2300 is performed during the curing time of the occlusion material. In another embodiment, the occlusion material is deposited within the implant, the delivery of stage 2300 performed during the curing time of the occlusion material.

In optional stage 2320, the occlusion material of stage 2310 comprises super-absorbable particles embedded in a fabric coupled to the delivered implant of stage 2300, optionally the fabric being bio-compatible. In one embodiment, the super-absorbable particles exhibit a swelling capacity of 1:10-1:200. In another embodiment, the fabric comprises polyethylene terephthalate fabric. In one embodiment, the fabric is wrapped around the material of the implant. The super-absorbable particles are arranged to expand responsive to inter-annulus fluids thereby occluding the annulus tear.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. An implant for repair of a spinal inter-vertebral disc, the implant comprising:
   a first section and a second section, each of said first section and said second section comprising:
   a support member section exhibiting a longitudinal axis, said support member section having a first face and a second face opposing said first face, said support member further having a distal end and a proximal end;
   a proximal securing member secured to said proximal end of said support member section and arranged to extend proximally thereof, said proximal securing member arranged in a deployed configuration to distend in the direction of said first face of said support member section; and
   a pair of inter-annulus support members, each of said pair of inter-annulus support members arranged on opposing sides of said longitudinal axis of said support member section along said proximal end, each of said pair of inter-annulus support members exhibiting a first end secured to the proximal end of said support member section, a second end and a link member coupling said first end to said second end,
   wherein each of said inter-annulus support members has a deployed configuration wherein the second end of each of said inter-annulus support members extends away from the longitudinal axis of said axial support member section, a first face of each of said inter-annulus support members generally facing said support member section and generally concavingly curved when viewed from the proximal end of said support member section, and a second face of each of said inter-annulus support members generally convexingly curved when viewed from the proximal end of said support member section, and
   wherein said support member section of said first section secured to said support member section of said second section such that the second face of said first section faces the second face of said second section.

2. The implant according to claim 1, wherein each of said pair of inter-annulus support members comprises a plurality of stacked layers, each of said plurality of stacked layers exhibiting a first end secured to the proximal end of said support member section, a second end and a link member coupling said first end to said second end, and
   wherein in the deployed configuration a first face of each of said inter-annulus support member layers generally faces said support member section and is generally concavingly curved when viewed from the proximal end of said support member section, and a second face of each of said inter-annulus support members is generally convexingly curved when viewed from the proximal end of said support member section.

3. The implant according to claim 1, wherein said proximal support member is constituted of a unitary member.

4. The implant according to claim 1, wherein said proximal securing member comprises an extending portion, which in the deployed configuration distends in the direction of said first face of said support member section.

5. The implant according to claim 4, wherein said support member sections, inter-annulus support members and proximal support member occlude 20%-95% of a target channel in a spinal annulus.

6. The implant according to claim 1, wherein said second face of said support member section of said first section is arranged to meet said second face of said support member of said second section.

7. The implant according to claim 1, wherein said support member section of each of said first section and said second section comprises an elastic member arranged to extend past the second surface of said support member section of said respective section, a far face of said elastic member of said first section secured to a far face of said elastic member of said second section, said elastic members providing elasticity to support Sagittal motion when deployed.

8. The implant according to claim 1, wherein each of said inter-annulus support members has a delivery configuration wherein said inter-annulus support members do not extend past a plane defined by the outer surfaces of said support member section.

9. The implant according to claim 8, wherein said proximal securing member exhibits a delivery configuration wherein said proximal securing member does not extend past a plane defined by the outer surfaces of said support member section.

10. The implant according to claim 1, wherein the implant is formed from a bio-compatible shape memory polymer.

11. The implant according to claim 1, further comprising an additive, the additive coupled to a portion of the implant, coated on a portion of the implant or impregnated into a portion of the implant.

12. The implant according to claim 11, wherein said additive comprises a diagnostic agent.

13. The implant according to claim 12 wherein said diagnostic agent comprises a radio-opaque material.

14. The implant according to claim 11, wherein said additive comprises a therapeutic agent.

15. The implant according to claim 14, wherein said therapeutic agent is selected from the group consisting of: antibiotics; antiproliferative, cytotoxic, and antitumor drugs including chemotherapeutic drugs; analgesic; antiangiogen; antibody; antivirals; cytokines; colony stimulating factors; proteins; chemoattractants; ethylenediaminetetraacetic acid (EDTA); histamine; antihistamine; erythropoietin; antifungals; antiparasitic agents; non-corticosteroid anti-inflammatory agents; anticoagulants; anesthetics; analgesics; oncology agents; cardiovascular drugs; vitamins and other nutritional supplements; hormones; glycoproteins; fibronectin; peptides including polypeptides and proteins; interferons; cartilage inducing factors; protease inhibitors; vasoconstrictors, vasodilators, demineralized bone or bone morphogenetic proteins; lipids; carbohydrates; proteoglycans; antiangiogenins; antigens; demineralised bone matrix (DBM); hyaluronic acid and salts and derivatives thereof; polysaccharides; cellulose compounds and derivatives thereof; antibodies; gene therapy reagents; genetically altered cells, stem cells including mesenchymal stem cells with transforming growth factor, and/or other cells; cell growth factors; type II collagen; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1); Lim Mineralization Protein-1 (LMP-1); cartilage; oxygen-containing components; enzymes; melatonin; vitamins; and nutrients.

16. The implant according to claim 11, wherein said additive comprises:
aprotinin; and
calcium ions.

17. The implant according to claim 11, wherein said additive comprises:
an anti-inflammatory agent.

18. The implant according to claim 17, wherein said anti-inflammatory agent comprises: inhibitors of a plurality of cytokines.

19. The implant according to claim 18, wherein said cytokines are selected from the group consisting of: interleukin 1 (IL-1), interleukin 6 (IL-6), interleukin 8 (IL-8), tumor necrosis factor-alpha (TNF-a), and metalloproteinases.

20. The implant according to claim 17, wherein said anti-inflammatory agent is selected from the group consisting of: tumor necrosis factor antagonists; Interleukin antagonists; and anti-inflammatory nutraceuticals.

21. The implant of claim 11, wherein said additive comprises growth factors.

22. The implant of claim 21, wherein said growth factors are selected from the group consisting of: transforming growth factors; insulin-like growth factors; platelet-derived growth factor; bone morphogenetic protein-2; bone morphogenetic protein-7; and growth/differentiation factor-5.

23. The implant according to claim 1, further comprising an occlusion material arranged to substantially occlude an annual tear in conjunction with said support member sections, said proximal securing members and said inter-annulus support members.

24. The implant according to claim 23, wherein said occlusion material comprises one of: super-absorbable particles embedded in fabric; and in-situ curing material.

25. An implant for repair of a spinal inter-vertebral disc, the implant comprising:
a first section and a second section, each of said first section and said second section comprising:
a support member section exhibiting a longitudinal axis, said support member section having a first face and a second face opposing said first face, said support member further having a distal end and a proximal end;
a proximal securing member secured to said proximal end of said support member section and arranged to extend proximally thereof, said proximal securing member arranged in a deployed configuration to distend in the direction of said first face of said support member section; and
a pair of inter-annulus support members, each of said pair of inter-annulus support members arranged on opposing sides of said longitudinal axis of said support member section along said proximal end, each of said pair of inter-annulus support members exhibiting a first end secured to the proximal end of said support member section, a second end and a link member coupling said first end to said second end,
wherein each of said inter-annulus support members having a deployed configuration wherein the second end of each of said inter-annulus support members extends away from the longitudinal axis of said axial support member section, a first face of each of said inter-annulus support members generally facing said support member section and generally concavingly curved when viewed from the proximal end of said support member section, and a second face of each of said inter-annulus support members generally convexingly curved when viewed from the proximal end of said support member section,
wherein said support member section of said first section secured to said support member section of said second section such that the second face of said first section faces the second face of said second section,
wherein each of said pair of inter-annulus support members comprises a plurality of stacked layers, each of said plurality of stacked layers exhibiting a first end secured to the proximal end of said support member section, a second end and a link member coupling said first end to said second end,
wherein in the deployed configuration a first face of each of said inter-annulus support member layers generally faces said support member section and is generally concavingly curved when viewed from the proximal end of said support member section, and a second face of each of said inter-annulus support members is generally convexingly curved when viewed from the proximal end of said support member section, and
wherein at least one of said plurality of stacked layers further comprises a protrusion at said second thereof arranged so as to arrest movement of an adjacent layer, at a predetermined point, caused by a force applied to the adjacent layer, said protrusion provided member and said adjacent layer thus cooperating under the force to act as a single layer.

26. An implant for repair of a spinal inter-vertebral disc, the implant comprising:
- a first section and a second section, each of said first section and said second section comprising:
  - a support member section exhibiting a longitudinal axis, said support member section having a first face and a second face opposing said first face, said support member further having a distal end and a proximal end;
  - a proximal securing member secured to said proximal end of said support member section and arranged to extend proximally thereof, said proximal securing member arranged in a deployed configuration to distend in the direction of said first face of said support member section; and
  - a pair of inter-annulus support members, each of said pair of inter-annulus support members arranged on opposing sides of said longitudinal axis of said support member section along said proximal end, each of said pair of inter-annulus support members exhibiting a first end secured to the proximal end of said support member section, a second end and a link member coupling said first end to said second end,
- wherein each of said inter-annulus support members having a deployed configuration wherein the second end of each of said inter-annulus support members extends away from the longitudinal axis of said axial support member section, a first face of each of said inter-annulus support members generally facing said support member section and generally concavingly curved when viewed from the proximal end of said support member section, and a second face of each of said inter-annulus support members generally convexingly curved when viewed from the proximal end of said support member section,
- wherein said support member section of said first section secured to said support member section of said second section such that the second face of said first section faces the second face of said second section,
- wherein each of said pair of inter-annulus support members comprises a plurality of stacked layers, each of said plurality of stacked layers exhibiting a first end secured to the proximal end of said support member section, a second end and a link member coupling said first end to said second end,
- wherein in the deployed configuration a first face of each of said inter-annulus support member layers generally faces said support member section and is generally concavingly curved when viewed from the proximal end of said support member section, and a second face of each of said inter-annulus support members is generally convexingly curved when viewed from the proximal end of said support member section, and
- wherein said support member section of said first section comprises an elastic member arranged to extend past the second surface of said support member section of said first section, said support member section of said second section secured to a far face of said elastic member of said first section, said elastic member providing elasticity to support Sagittal motion when deployed.

* * * * *